United States Patent [19]

Harris et al.

[11] Patent Number: 4,923,987

[45] Date of Patent: May 8, 1990

[54] PROCESS FOR THE PREPARATION OF NITROMETHYLENE HETEROCYCLIC COMPOUNDS

[75] Inventors: Martin Harris, Sittingbourne; Graham Heyes, Durham; Arthur Jackson, Washington, all of England

[73] Assignee: E. I. du Pont de Nemours and Company, Wilmington, Del.

[21] Appl. No.: 223,874

[22] Filed: Jul. 25, 1988

[51] Int. Cl.$^5$ .................. C07D 277/10; C07D 279/06
[52] U.S. Cl. ........................................ 544/53; 544/54; 548/200; 548/146
[58] Field of Search .................. 544/54, 53; 548/200, 548/146

[56] References Cited

U.S. PATENT DOCUMENTS 4,052,388 10/1977 Powell .................................. 544/54
4,501,742 2/1985 Harris .................................. 544/54
4,532,322 7/1985 Jackson et al. ...................... 544/54

FOREIGN PATENT DOCUMENTS 1513951 6/1978 United Kingdom .
1576120 10/1980 United Kingdom .

*Primary Examiner*—John M. Ford
*Attorney, Agent, or Firm*—William H. Hamby

[57] ABSTRACT

The invention provides a process for the preparation of nitromethylene heterocyclic compounds of general formula

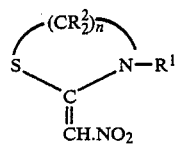

wherein $R^1$ represents a hydrogen atom or a formyl or acetyl group, each moiety $R^2$ is independently selected from hydrogen atoms and $C_{1-4}$ alkyl and benzyl groups, and n is 2 or 3, which process comprises reacting an alkali metal methylnitrodithioacetate with a compound of formula $$H_2N-(CR_2^2)_n-OSO_3H \qquad (II)$$

wherein $R^2$ and n are as defined above, optionally followed by conversion of the resulting compound of Formula I wherein $R^1$ is hydrogen to the corresponding compound of Formula I wherein $R^1$ is formyl or acetyl. Certain compounds of Formula I are known insecticidally active compounds.

7 Claims, No Drawings

PROCESS FOR THE PREPARATION OF NITROMETHYLENE HETEROCYCLIC COMPOUNDS

BACKGROUND OF THE INVENTION

This invention relates to a process for the preparation of nitromethylene heterocyclic compounds.

UK Patent Specification No. 1,513,951 discloses a group of pesticidally, particularly insecticidally and acaricidally, active nitromethylene derivatives of oxazine and thiazine. UK Patent Specification No. 1,576,120 discloses the utility in combating insect pests of rice crops of a class of nitromethylene heterocyclic compounds of formula

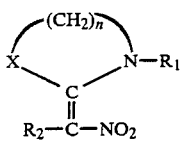

wherein n is 2 or 3, X inter alia represents S, $R_1$ inter alia represents a hydrogen atom and $R_2$ inter alia represents a hydrogen atom, 2-nitromethylenetetrahydro-2H-1,3-thiazine being specifically exemplified.

U.S. Pat. No. 4,052,388 discloses 3-acetyl-2-nitromethylene-tetrahydro-2H-1,3-thiazine and its insecticidal activity. EP-A-117577 discloses 3-formyl-2-nitromethylene-tetrahydro-2H-1,3-thiazine and its pesticidal, particularly insecticidal activity. The preparation of the 3-acetyl- and 3-formyl-derivatives is via 2-nitromethylene-tetrahydro-2H-1,3-thiazine.

According to UK Patent Specification No. 1,513,951, 2-nitromethylene-tetrahydro-2H-1,3-thiazine may be prepared by either of two methods:

Method A: treating nitroketene dimethyl mercaptole (R. Gompper & H. Schaefer, *Chemische Berichte*, 100, 591 (1967)) with 3-amino-1-propanethiol (S. D. Turk, et al., *J. Org. Chem.*, 27, 2846 (1962)); and Method B: treating 5,6-dihydro-2-(methylthio)-4H-1,3-thiazine (A. F. McKay et al., *J. Am. Chem. Soc.*, 80, 3339 (1958)) with an alkyl, e.g., ethyl, nitroacetate (S. Zen et al., *Kogyo Kagaku Zasshi*, 74, 70 (1971)) in the presence of a catalytic amount of zinc ion (e.g., zinc chloride) to form the alkyl nitro (tetrahydro-2H-1,3-thiazine-2-yl-idene) acetate, which is hydrolyzed with a base and decarboxylated by acidification to give the desired product.

In EP-A-127413 it is indicated that Method A has the disadvantage that 3-amino-1-propanethiol is not readily accessible, being an expensive material, and overall yield is only moderate, and that Method B suffers from the disadvantage that ethyl nitroacetate is not available in commercial-scale quantities.

EP-A-127413 itself discloses a process for the preparation of compounds of formula

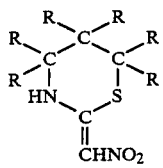

where each R is hydrogen or an appropriate aromatic or aliphatic substituent, the method comprising reacting together a sulphur donor, 1,1-bis(methylthio)-2-nitroethene and a compound of the formula

where each R is as defined above. Preferably, each R is independently hydrogen or $C_{1-4}$ alkyl and more preferably each R is hydrogen. The sulphur donor may be any suitable source of sulphur, for example, sulphur itself, a sulphide, a hydrosulphide or hydrogen sulphide. Preferably, the sulphur donor is an ammonium or alkali metal sulphide or hydrosulphide, e.g., sodium sulphide.

In the process of EP-A-127413, two mols of methanethiol are produced per mol of desired end product. There has now surprisingly been developed an improved process wherein in the preparation of such products the stoichiometry requires only one mol of methanethiol to be produced per mol of desired end product.

SUMMARY OF THE INVENTION

According to the present invention there is provided a process for preparation of a nitromethylene heterocyclic compound having insecticidal activity and of general formula

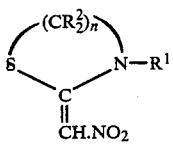

wherein $R^1$ represents a hydrogen atom or a formyl or acetyl group, each moiety $R^2$ is independently selected from hydrogen atoms and $C_{1-4}$ alkyl and benzyl groups, and n is 2 or 3, which process comprises reacting an alkali metal methylnitrodithioacetate with a compound of formula

wherein $R^2$ and n are as defined above, optionally followed by conversion of the resulting compound of Formula I wherein $R^1$ is hydrogen to the corresponding compound of Formula I wherein $R^1$ is formyl or acetyl.

Preferably each moiety $R^2$ is hydrogen. It is also preferred for n to be 3.

DETAILED DESCRIPTION OF THE INVENTION

Conversion of compounds of Formula I wherein $R^1$ is hydrogen to the corresponding compounds of Formula I wherein $R^1$ is formyl or acetyl may be achieved by known methods, e.g., as described in EP-A-117577 and in U.S. Pat. No. 4,052,388 with reference to UK Patent Specification No. 1,513,951.

The reaction of the alkali methal methylnitrodithioacetate with the compound of Formula II may conveniently be effected at a temperature in the range 0° to 120° C., but in order to achieve an advantageous combination of fast reaction time and acceptable yield, reaction is preferably effected at a temperature in the range of 60° to 80° C.

Those skilled in the art will appreciate that for stability reasons the alkali metal methylnitrodithioacetate has to be kept at a pH of at least 7.

The alkali metal methylnitrodithioacetate is preferably potassium methylnitrodithioacetate. In the process of the invention preferably the compound of Formula II is added to an aqueous solution of potassium methylnitrodithioacetate having a pH in the range 7.3 to 7.7.

Reaction of the alkali metal methylnitrodithioacetate with the compound of Formula II may be effected in aqueous solution in the presence or absence of a water-immiscible cosolvent. Suitable water-immiscible cosolvents include aromatic solvents, such as benzene, toluene, xylenes and chlorobenzene, and liquid chlorinated alkanes, e.g., $C_{2-4}$ di- and trichloroalkanes.

Examples of such chlorinated alkanes include 1,2-dichloroethane (b.p. 83° C.), 1,1,2-trichloroethane (b.p. 113° C. to 114° C.), 1,1,1-trichloroethane (b.p. 74° C. to 75° C.), 1,1-dichloropropane (b.p. 87° C.), 1,2-dichloropropane (b.p. 95° C. to 96° C.) and 1,3-dichloropropane (b.p. 125° C.). Other such halogenated hydrocarbons will be immediately apparent to those skilled in the art. 1,2-Dichloroethane has been found to be very suitable.

The molar ratio of the alkali metal methylnitrodithioacetate to the compound of Formula II is preferably in the range 1.5:1 to 1:1.5, more preferably 1.2:1 to 1:1.2.

Potassium methylnitrodithioacetate may conveniently be prepared by reaction of dipotassium nitrodithioacetate with a substantially equimolar amount of dimethylsulphate, in the presence of a phase-transfer catalyst, such as benzyl trimethyl ammonium chloride.

The preparation of dipotassium nitrodithioacetate is described by R. Gompper and H. Schaefer, *Chemische Berichte*, 100, 591 (1967). It is important that the dipotassium nitrodithioacetate is not allowed to become dry as it is pyrophoric.

A compound of Formula II may readily be prepared from the corresponding hydroxy compound of Formula

$$H_2N-(CR_2^2)_n-OH \qquad (III)$$

wherein $R^2$ and n are as defined above, and sulphuric acid.

The invention will be further understood from the following illustrative Examples.

EXAMPLE 1

Preparation of 2-nitromethylene-tetrahydro-2H-1,3-thiazine (a) Preparation of potassium methylnitrodithioacetate Dipotassium nitrodithioacetate was dissolved in a solution of benzenetrimethylammonium chloride (1.5 g) in water (167 ml). To the resulting solution was added, dropwise, over 60 minutes at a temperature maintained in the range 18° to 22° C., dimethyl sulphate (31 g, 0.246 mol). A small amount of 1,1-bis-(methylthio)-2-nitroethene precipitated out. The solution was filtered to remove precipitated material, leaving a solution of potassium methylnitrodithioacetate, pH 10 or greater, which remained stable at below 0° C. for 24 hours.

(b) Preparation of 2-nitromethylene-tetrahydro-1H-1,3-thiazine

To the solution product of step (a), the solution of potassium acid (2 molar, about 2 ml) until the pH of the solution was in the range 7.3 to 7.7. 3-Aminopropyl sulphate (39 g) was added to the solution, followed by sodium hydroxide (9.9 g), and the reaction mixture was heated to 65° C. over 45 minutes and maintained at that temperature for a further 60 minutes, after which time evolution of methanethiol had effectively ceased. 1,2-Dichloroethane (100 ml) was added over 15 minutes, while the reaction temperature was increased to reflux (68° to 72° C.). The temperature was maintained at reflux for a further 2½ hours.

After cooling to 35° C., the mixture was filtered to remove inorganic solids, the mixture was allowed to separate into organic and aqueous phases and the organic phase was separated off. The aqueous phase was washed with dichloromethane (4×100 ml), and the combined organic phases were dried (MgSO4) and evaporated to dryness in a rotary evaporator to give 2-nitromethylene-tetrahydro-2H-1,3-thiazine as a red oil which slowly solidified on standing to give a yellow solid (23.8 g; circa 80% purity; circa 40% w yield based on nitromethane).

EXAMPLE 2

Preparation of 3-formyl-2-nitromethylene-tetrahydro-2H-1,3-thiazine (c.f. Example 1 of EP-A-117577)

Triethylamine (5.2 ml) was added to a stirred solution of 2-nitromethylene-tetrahydro-2H-1,3-thiazine (3.2 g) in dry dichloromethane (30 ml) at ambient temperature under nitrogen.

The solution was then cooled to −20° C. and formic acetic anhydride (5.6 g) in dry dichloromethane (30 ml) was added dropwise with stirring. The temperature of the solution was then allowed to rise to 0° C. with continued stirring over a period of 30 minutes. The reaction was then poured into a mixture of ice and 2M HCL (10 ml). The organic layer was separated, washed with 2M HCL (50 ml) followed by water, and dried (MgSO4). The solvent was then removed under reduced pressure and the residue was recrystallized from chloroform to yield the desired product as a yellow crystalline solid, m.p. 138°–140° C.

EXAMPLE 3

Preparation of 3-acetyl-2-nitromethylene-tetrahydro-2H-1,3-thiazine (a) Preparation of 1-nitro-tetrahydro-2H-1,3-thiazin-2-yl-idene)-2-pentanone (c.f. Example 41 of UK Patent Specification No. 1,513,951

A mixture of 5.0 g of 2-nitromethylene-tetrahydro-2H-1,3-thiazine and 5.5 g of butyric anhydride was stirred under nitrogen at 85°–90° C. for 5 hours. The resulting dark oil was cooled, diluted with methylene chloride, washed successively with concentrated ammonium hydroxide, water and saturated salt solution, then dried with sodium sulphate and concentrated under reduced pressure to leave a dark oil which was chromatographed on "Florosil" (R.T.M.) using methylene chloride as eluent to give a solid which was washed with hexane to leave 1-nitro-1-(tetrahydro-2H-1,3-thiazin-2-yl-idene)-2-pentanone as a yellow solid, m.p. 54°–58.5° C.

(b) Preparation of 3-acetyl-2-nitromethylene-tetrahydro-2H-1,3-thiazine (c.f. U.S. Pat. No. 4,052,288)

A solution of 23 g of 1-nitro-1-(tetrahydro-2H-1,3-thiazin-2-yl-idene)-2-pentanone in 200 ml of monoglyme was added dropwise at 0° C. to a suspension of 4.65 g of a 57% sodium hydride/mineral oil dispersion in 100 ml of monoglyme. The stirred mixture was allowed to warm to room temperature and stirred overnight. A solution of 8.2 g of acetyl chloride in 50 ml of monoglyme was added dropwise to the reaction at 0° C. The resulting mixture was stirred for one hour at 0° C., then allowed to warm to room temperature and stirred for 30 minutes. The mixture was diluted with chloroform and extracted with 10% sodium hydroxide solution. The organic phase was separated, washed with water, then with saturated sodium chloride solution, and dried Na$_2$SO$_4$), and the solvent was evaporated under reduced pressure. The resulting liquid was chromatographed, using a wet column with silica gel. As eluent, there was first used 2 litres of a 98/2 chloroform/acetone mixture, then a 95/5 chloroform/acetone mixture was used. Three fractions were obtained. The last fraction was triturated with ether, then cooled, to give a solid yellow product, 3-acetyl-2-nitromethylene-tetrahydro-2-H-1,3-thiazine, m.p. 91°–92.5° C.

What is claimed is:

1. A process for the preparation of a nitromethylene heterocyclic compound of formula

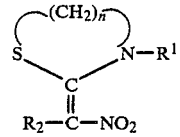

wherein $R^1$ represents a hydrogen atom, each moiety $R^2$ is independently selected from hydrogen atoms and $C_{1-4}$ alkyl and benzyl groups, and n is 2 or 3, which process comprises reacting an alkali metal methylnitrodithioacetate with a compound of formula

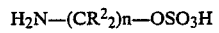

wherein $R^2$ and n are as defined above, to produce a compound of Formula I wherein $R_1$ is hydrogen.

2. A process according to claim 1 wherein each moiety $R^2$ is hydrogen.

3. A process according to claim 1 or 2 wherein n is 3.

4. A process according to claim 2 wherein reaction is effected at a temperature in the range of 60° to 80° C.

5. A process according to claim 3 wherein reaction is effected at a temperature in the range of 60° to 80° C.

6. A process according to claim 1, 2, 5 or 4 wherein the alkali metal methylnitrodithioacetate is potassium methylnitrodithioacetate.

7. A process according to claim 6 wherein the compound of Formula II is added to an aqueous solution of potassium methylnitrodithioacetate having a pH in the range of 7.3 to 7.7.

* * * * *